United States Patent [19]

Price

[11] Patent Number: 4,705,910

[45] Date of Patent: Nov. 10, 1987

[54] TETRAPLOID CORN AND METHODS OF PRODUCTION

[75] Inventor: Steven C. Price, Cleveland Heights, Ohio

[73] Assignee: The Standard Oil Company, Cleveland, Ohio

[21] Appl. No.: 777,374

[22] Filed: Sep. 18, 1985

[51] Int. Cl.$^4$ .............................................. A01H 1/02
[52] U.S. Cl. .................................... 800/1; 47/DIG. 1
[58] Field of Search .................. 47/58, DIG. 1; 800/1

[56] References Cited

PUBLICATIONS

Corn & Corn Improvement, Sprague, 1977, Amer. Soc. Agron., Madison, Wisc., pp. 235-236.
Rice, J. S. and J. W. Dudley, Crop Science, 14:390-393, 1974.
Sarkar, K. R. and P. Paria, *Indian Journal of Experimental Biology*, 18:985-989, 1980.
Randolph, L. F., *Proc. N.A.S.*, 18:222-229, 1932.
Randolph, L. F., *J. of Agricultural Research*, 50(7): 591-605, 1935.
Randolph, L. F., *J. of Agricultural Research*, 69:47-76, 1944.
Dudley, J. W. and D. E. Alexander, *Crop Science*, 9:613-615, 1969.

*Primary Examiner*—Robert E. Bagwill
*Attorney, Agent, or Firm*—Teresan W. Gilbert; Joseph G. Curatolo; Larry W. Evans

[57] ABSTRACT

A hybrid tetraploid corn seed and a process for its production are disclosed. Upon growth, the hybrid tetraploid corn seed yields a hybrid tetraploid corn plant, which exhibits superior biomass yield when compared to hybrid diploid corn plants. The hybrid seed is produced by crossing a first inbred line of tetraploid corn with a non-identical second inbred line of tetraploid corn to form at least one hybrid tetraploid seed.

36 Claims, No Drawings

TETRAPLOID CORN AND METHODS OF PRODUCTION

BACKGROUND OF THE INVENTION

This invention relates generally to the production of corn, and particularly to the production of inbred and hybrid tetraploid corn.

In order to understand and appreciate the significance of the claimed invention and the techniques described herein, it is necessary to understand certain basic principles of genetics and plant breeding.

The genetic information of higher plants is contained in chromosomes located inside the nucleus of individual plant cells. This is called the "genome" of the plant. The genome of plants usually exists within each cell as sets of similar or homologous chromosomes. The chromosomes contain the basic units of heredity, the gene. Genes occupy fixed positions on the chromosomes, and each gene has a specific influence on the expression of a particular characteristic or characteristics of the plant. Alternative forms of the same genes are known as alleles, and different alleles of a gene may be found on homologous chromosomes. If homologous chromosomes contain the same alleles for a particular gene, the plant is homozygous for that gene and the characteristic that it controls. If homologous chromosomes contain different alleles for the same gene, the plant is heterozygous for that gene and the characteristic that it controls.

The number of chromosome sets in the cell of a plant is called the plant's "ploidy" and is often designated a multiple of "N" where "N" denotes the number of chromosomes per set. A plant with N chromosomes in its cell nucleus is termed "haploid," a plant with 2N chromosomes is termed "diploid," and a plant with 4N chromosomes is termed "tetraploid," and so on. The term "polyploid" refers to multiple chromosome sets in excess of two. The numerical value of N differs from species to species. In corn, N is normally equal to 10. Hence, diploid corn has 2N or 20 chromosomes, tetraploid corn has 4N or 40 chromosomes, and polyploid corn has 3 or more sets of N chromosomes.

Gametes or reproductive cells have nuclei that ordinarily contain half of the total sets of chromosomes and, therefore, one half of the number of chromosomes. Thus, if a plant is diploid, its gametes will be haploid; if it is tetraploid, its gametes will be diploid. The fusion of gametes from a male parent and a female parent produces a zygote, which develops into a seed.

The corn that conventionally has been grown for human or animal food, or as a source of raw materials or chemicals, is diploid (2N=20). Production of biomass by diploid corn, in the form of grain (the ears) and stover (the remainder of the plant), has conventionally been increased by the use of fertilizers, pesticides, and selective breeding. Although the application of fertilizers and the elimination of insect pests have resulted in increased yields of biomass, the effectiveness of all of these methods is limited by the genetic makeup of the plant.

For this reason, much research in improving corn production has concentrated on selective breeding. Selective breeding is conducted by selecting plants that have desirable traits, such as resistance to disease, increased production of biomass, or high fertility, and inbreeding those plants or outcrossing them with other plants having desirable characteristics.

Inbreeding is a technique that produces maximum genetic uniformity in a genetically variable, cross-pollinated species, such as corn. Inbred lines are derived by a process of self-pollination and selection, usually over 5 or more generations, so that allelic pairs of genes on homologous chromosome pairs are homozygous or identical. The degree of inbreeding (homozygosity) in a line is approached at the rate of about 50% per generation so that by the second generation, plants are about 75% homozygous and by the sixth generation about 98% homozygous. Thereafter, all plants derived from self-pollination, sibling pollination, or random crossing with others in the inbred line theoretically should be essentially genetically identical and, therefore, should be essentially homozygous and uniform in appearance. However, the determination of whether a uniform, stable, and essentially homozygous line exists requires the putative inbred line to be field tested and examined for variation in its significant characteristics. If the degree of variation is unacceptable, i.e., too high, the process of self-pollination and selection must be continued for additional generations until the degree of variation in the line's significant characteristics is acceptable.

Although inbreeding results in genetic uniformity, it also results in a reduction in performance, yield, and plant size for species that normally reproduce by cross-pollination. This reduction is known as inbreeding depression and is the reason that the uniform inbred lines are not grown as a commercial crop.

Outcrossing or hybridization involves cross-pollination of plants differing in genetic constitution. Thus, a hybrid is the progeny of genetically unlike parents. Hybridization results in the progeny expressing a variety of characteristics, and the plant breeder will select plants expressing desirable characteristics for further breeding. Some examples of desirable characteristics sought through hybridization are increased yield, resistance to diseases and insects, faster maturity, and specific changes in the size, shape, and height of the plant. Random hybridization, however, produces a commercially undesirable level of variation in the genetic makeup and characteristics of the resulting plants.

The principal technique used for the production of uniform plant populations that do not show inbreeding depression is the hybridization of two inbred lines to produce hybrid seeds which, upon planting and growth, produce uniform first generation ($F_1$) hybrid plants. Because of hybrid vigor, maximum yield as well as uniformity is achieved.

The development of the desired hybrid seeds is a specialized and highly skilled procedure. Crosses of many different inbred lines must be done, the hybrid seeds must be grown, and the plants must be evaluated for desired characteristics. Often, a program to develop a new hybrid seed starts with the development of new inbred lines, which are then crossed to determine which ones will produce the desired hybrid. A great many different inbred lines may be evaluated. The total time to develop a new hybrid seed can be as much as 7–10 years.

Once the inbred lines are developed and the best ones are selected by evaluating the hybrids they produce, new hybrid seeds are obtained each generation by crossing the originally selected inbred parents. The desired hybrid cannot be reproduced from self-pollination, or by crossing with another $F_1$ hybrid because the recombination of genes will produce progeny that are extremely variable in maturity, quality, and yield. As a result, farmers usually purchase the hybrid seeds used to produce $F_1$ hybrid plants from a commercial seed company.

In diploid corn, improvements by selective breeding have been slow, since only one to three generations of corn may be propagated each year. Therefore, relatively minor improvements in diploid corn, such as increases in biomass, have been obtained only after years of rigorous work.

Although tetraploid corn has been known for approximately 50 years, it has been cultivated for the purposes of curiosity and cytological and genetic studies rather than for the production of grain or large quantities of biomass. Thus, there is limited discussion in the scientific literature of the grain or biomass production characteristics of tetraploid corn, and statements about these characteristics have been made without supporting data. One report concludes that tetraploid corn is inferior to diploid corn on the basis of grain yield. Such statements provide little incentive for developing inbred lines of tetraploid corn for the purpose of producing hybrid tetraploid corn seed for commercial uses. The inventor is unaware of the development of any inbred lines (as defined herein) of tetraploid corn prior to the present invention.

Tetraploid corn was studied as early as the 1930's. In 1932, L.F. Randolf reported on the use of high temperature to induce tetraploidy in corn. Randolph, L.F., *Proc. N.A.S.* 18:222-229, 1932. In 1935, Randolph stated that tetraploids ". . . are of about the same height and have a similar habit of growth [as diploid corn]. However, their stalks are thicker and sturdier and the leaves are somewhat broader and thicker . . . the ears and kernels of tetraploid maize are distinctly larger than those of comparable diploid stocks." Randolph L. F., *J. of Agricultural Research* 50(7):591-605, 1935. However, Randolph presented no quantitative data to substantiate these statements. In 1944, Randolph published data that supported his statement with respect to leaf characteristics only. Randolph, L. F., *J. of Agricultural Research* 69:47-76, 1944.

Characteristics of several types of tetraploid corn were examined in the 1950's and 1960's by Dudley and Alexander at the University of Illinois. Their findings as to grain yield, seed set, plant height, ear height, weight per 100 kernels, number of kernel rows, and ear length of tetraploid corn were reported in Dudley, J. W. and D. E. Alexander, *Crop Science* 9:613-615, 1969. This study concluded that the highest grain yield obtained from the tetraploids was not competitive with good diploid hybrids. No diploids were included in the experiment for comparison.

In 1974, Rice and Dudley reported on inbreeding depression in tetraploid corn resulting from selfing and from full-sib mating. Rice, J. S. and J. W. Dudley, *Crop Science* 14:390-393, 1974. However, they reported their data on a population basis rather than for individual lines. No data on the variation of important characteristics were reported for individual lines, which would have been necessary to demonstrate the creation of inbred lines.

Thus, although tetraploid corn has been documented for over 50 years, the inventor is unaware of any published reports supported by data of either inbred lines (as defined herein) of tetraploid corn or hybrid tetraploid corn produced by crossing inbred lines, nor is the inventor aware of any published data documenting that tetraploid corn is superior to diploid corn for grain, stover, and whole plant production. In fact, as indicated above, the published work of some breeders indicates that yields from tetraploid corn are inferior to that of good diploid hybrids.

From the comparison of certain populations of tetraploid corn and their first generation intercross progeny with certain lines of hybrid diploid corn, it has been discovered that tetraploid corn plants show a biomass yield superior to diploid plants. Such increase in yield is on the order of 5-20%. This unexpected and surprising discovery provided the motivation to develop inbred lines of tetraploid corn that may be crossed to produce hybrid seeds and plants. Because of the greater biomass yields, hybrid tetraploid corn plants will be attractive as a source of food for livestock, as silage, and as raw material for the production of biomass-derived chemicals, such as ethanol.

SUMMARY OF THE INVENTION

It is an object of this invention to provide a process for producing an inbred line of tetraploid corn by selecting plants having desired characteristics from a population of heterozygous tetraploid corn plants, self-pollinating the selected plants to produce seeds, growing the seeds to produce progeny, selecting plants having desired characteristics from the progeny, and repeating the steps of self-pollinating, growing, and selecting until an inbred line of tetraploid corn having the desired characteristics is developed.

It is another object of this invention to provide a process for producing a seed of an inbred line of tetraploid corn by self-pollinating an inbred line of tetraploid corn and harvesting a seed produced by the self-pollinating.

It is an additional object of the present invention to provide processes for producing a hybrid tetraploid corn seed. In one embodiment, a hybrid tetraploid corn seed is produced by crossing a first inbred line of tetraploid corn with a nonidentical second inbred line of tetraploid corn to produce a seed and harvesting the seed. In another embodiment, a hybrid tetraploid corn seed is produced by developing inbred lines of tetraploid corn which, upon cross-fertilization, yield $F_1$ hybrid seeds that produce hybrid tetraploid corn plants having desired characteristics, crossing any two nonidentical lines of the inbred lines to produce a $F_1$ hybrid seed, and harvesting the seed. In a third embodiment, a hybrid tetraploid corn seed is produced by selecting plants having desired characteristics from a population of heterozygous tetraploid corn plants, selfpollinating the selected plants to produce seeds, growing the seeds to produce progeny, selecting plants having desired characteristics from the progeny of the self-pollinated plants, repeating the steps of self-pollinating, growing, and selecting a sufficient number of generations to develop inbred lines of tetraploid corn having desired characteristics, crossing one of the inbred lines with another of the inbred lines, the crossed inbred lines being nonidentical, to produce a seed, and harvesting the seed.

It is still another object of this invention to provide a process for producing a hybrid tetraploid corn plant by crossing a first inbred line of tetraploid corn with a nonidentical second inbred line of tetraploid corn to produce a hybrid seed and harvesting and growing the hybrid seed to produce a hybrid plant.

It is a further object of the present invention to provide an inbred line of tetraploid corn, a seed of an inbred line of tetraploid corn, a hybrid tetraploid corn seed, a hybrid tetraploid corn plant, and a hybrid tetraploid corn zygote.

Additional objects and advantages of the invention will be set forth in part in the description that follows, and in part will be obvious from the description, or may be learned from the practice of the invention. The objects and advantages may be realized and attained by means of the instrumentalities and combinations particularly pointed out in the appended claims.

DETAILED DESCRIPTION OF THE INVENTION

Reference will now be made in detail to the presently preferred embodiments of the invention, which, together with the following examples, serve to explain the principles of the invention.

As noted above, the present invention relates to an inbred line of tetraploid corn, a seed for such an inbred line, a hybrid tetraploid corn plant, a hybrid tetraploid corn seed, and processes for their production. As used herein, the term "inbred line" or "inbred lines" shall mean a group of plants from a common ancestory which are essentially homozygous and are truebreeding (uniform and stable) for all of their agronomically important characteristics. The term "hybrid" or "hybrids" means the progeny of a cross between genetically unlike parents and, in the context of the present invention, means the first generation progeny ($F_1$) of a cross between two inbred lines.

The inbred line of tetraploid corn of the present invention and the seed for that line are distinguished from other types of tetraploid corn and seeds in that they are essentially homozygous and are true-breeding (uniform and stable) for all of their agronomically important characteristics. In preferred embodiments of the present invention, the inbred line has the characteristics of the lines designated as SX-4-2, SX-4-4, SX-4-16-2, SX-4-32-1, SX-4-33-4-2, SX-5-6, SX-5-11, SX-5-9-1-2, SX-5-13-3, SX-5-14-1-2, SX-6-3, and SX-6-15-2-1. which are highly fertile (at least 80% seed set) inbred lines of tetraploid corn developed by the present inventor. Similarly, the preferred seeds of inbred tetraploid corn of the present invention have the characteristics of the seeds of the so-designated lines. Further information regarding these inbred lines and seeds may be found in certificates filed with the U.S Variety Protection Office U.S. Plant Variety Protection Certificates Nos. 8400117, 8400116, 8500048, 8500049, 8500047, 8400114, 8400110, 8500045, 8500046, 8500051, 8500044, 8400118, and 8500050, respectively, issued on Feb. 28, 1986 (Nos. 8400110, 8400117), Ma. 31, 1986 (Nos. 8500046-8500049), and Oct. 31, 1986 (Nos. 840014, 8400116, 8400118, 8500045, 8500050, 8500051), the disclosures of which are hereby incorporated by reference. Seed samples of each line are on deposit with the Plant Variety Protection Office, U.S. Department of Agriculture, 10301 Baltimore Blvd., Beltsville, Md. 20705 in conjunction with each of the referenced applications.

The inbred lines of the present invention are produced by techniques known in the art. In a preferred embodiment, the inbred lines of tetraploid corn of the present invention are produced by the technique of continued self-fertilization, accompanied by selection. In particular, the inbred lines may be produced by the following method:

(a) selecting plants having desired characteristics from a population of heterozygous tetraploid corn plants;

(b) self-pollinating the selected plants to produce seeds;

(c) growing the seeds to produce progeny;

(d) selecting plants having the desired characteris tics from the progency; and (e) repeating the steps of self-pollinating, growing, and selecting for a sufficient number of generations to de velop essentially homozygous plants having the desired char acteristics.

The initial plants may be selected from any population of heterozygous tetraploid corn plants. In a preferred embodiment, the original plants are selected from breeding stock designated "Synthetic B," "Synthetic OP," and "Synthetic CD." These populations may be obtained from the University of Illinois or may be created by following the methods described by J. W. Dudley and D. E. Alexander in *Crop Science*, 9:4 613–615, 1969, which is hereby incorporated by reference. The stocks are very heterogeneous populations and are not inbred lines.

Plants grown from seeds of heterozygous populations may be evaluated by techniques well known in the art and may be selected on the basis of any desired characteristic that may be of interest to the breeder. Such characteristics include, but are not limited to, biomass yield, grain yield, stover yield, seed set, percent oil, standability, insect resistance, pesticide resistance, drought tolerance, and salinity tolerance. In a preferred embodiment, the desired characteristic is biomass yield, and in a particularly preferred embodiment, the desired characteristic is biomass yield superior to that of high biomass yielding diploid corn hybrids. As used herein, the term "biomass yield" means the total amount of above ground plant material; i.e., stalk, leaves, grain, husks, cobs, tassels, and the like. Further, the terms "biomass yield superior to" or "superior biomass yield" mean a higher biomass yield as measured by comparing average weight.

The initially selected tetraploid corn plants are self-pollinated, using techniques well-known in the art. The seeds are recovered and planted. The resulting plants are then evaluated for the characteristic or characteristics being sought and those showing the desired characteristic are again self-pollinated, and the seeds are harvested and planted. This process is repeated a sufficient number of generations until inbred lines having the desired characteristic or characteristics are developed. For diploid plants, it is usually necessary for this process to be repeated for at least five generations; for tetraploid plants, the development of inbred lines can also be expected to take at least five generations and perhaps more. In the course of developing inbred lines, the biomass, grain, and stover yield will generally decrease due to inbreeding. Thus, when the desired characteristics are biomass, grain, or stover yield, the comparisons will be made with inbred diploid corn lines.

Inbred lines of tetraploid corn are used to produce hybrid tetraploid corn seeds. The process for producing such seeds involves crossing specially selected, nonidentical inbred lines to produce seeds, which, upon planting, would yield hybrid tetraploid corn having desired characteristics. Such desired characteristics would include, but are not limited to, superior biomass yield, superior grain yield, and/or superior stover yield when compared to high yielding diploid hybrids. Such desired characteristics would also include, but are not limited to, insect resistance, pesticide resistance, drought resistance and tolerance for high salinity soil conditions. Such characteristics would be determined by the nature of the inbred lines and by trial crosses of various inbred lines to produce hybrid plants, which would then be evaluated by techniques well-known in the art. It is often desirable to select the inbred lines for high fertility in order to facilitate the yield of hybrid seeds. Preferred inbred lines for use in such crosses would be the following: SX-4-2, SX-4-4, SX-4-16-2, SX-4-32-1, SX-4-33-4-2, SX-5-6, SX-5-11, SX-5-9-1-2, SX-5-13-3, SX-5-14-1-2, SX-6-3, SX-6-15-2-1.

Upon growth, the hybrid seeds would produce hybrid plants with selected characteristics. In a particularly preferred embodiment, the selected characteristic is biomass yield superior to that of high biomass yielding diploid corn hybrids.

A hybrid tetraploid zygote could also be produced by crossing nonidentical inbred lines of tetraploid corn to form a hybrid tetraploid zygote. A seed could then be produced from the zygote.

The invention will further be illustrated by the following examples, although it will be understood that these examples are included merely for purposes of illustration and are not intended to limit the scope of the invention. Example I illustrates the superior biomass yield of tetraploid corn according to the present invention as compared to diploid corn. Examples II-IV illustrate the development of representative inbred lines of tetraploid corn according to the present invention. In particular, Example II shows the development of inbred tetraploid corn line X-4-2, which is the subject of U.S. Plant Variety Protection Certificate application No. 8400117, from tetraploid corn population Synthetic B. Example III shows the development of inbred tetraploid corn line X-5-6, which is the subject of U.S. Plant Variety Protection Certificate application No. 8400114, from tetraploid corn population Synthetic OP. Example IV shows the development of inbred tetraploid corn line X-6-3, which is the subject of U.S. Plant Variety Protection Certificate application No. 8400118, from tetraploid corn population Synthetic CD. Example V illustrates the production of a hybrid tetraploid corn plant and seed by crossing X-5-6 with X-6-3.

EXAMPLE I

Materials and Methods

Heterozyqous wild type tetraploid corn populations Synthetic B, OP, CD, ET, and RT were compared to hybrid diploid lines S-57 and S-39. Synthetic B, OP, and CD were obtained from the University of Illinois. Synthetic ET and RT were obtained from Cornell University, and S-57 and S-39 were obtained from the Sohio Agricultural Products Division of Sohio Chemical Corporation. The growth and final stover yield of these plants were compared in two randomized complete block design experiments done in the same year. One was at Sagamore Hills, Ohio. The other was at Greensburg, Ill.

At the Ohio location, tetraploid populations synthetic B, OP, and CD and hybrid diploid lines S-57 and S-39 were planted on the 5th of June. The planting density was equivalent to 14,000 plants per acre, which was obtained by planting in 30 foot rows, at 1 foot spacings between plantings and a 36" spacing between the rows. Each block consisted of 1 row of each line or population; the blocks were replicated three times. The soil at this location is very rocky, and has a low soil organic content. On June 15, the planting was fertilized with 12-12-12 (a mixture of 12% nitrogen, 12% phosphorus, and 12% potassium) at 75 lb./acre. No herbicides were used; weeding was done by hand. On July 23, leaf area measurements were taken. This was accomplished by measuring the width and length of the 7th leaf, and multiplying by the total number of leaves. Grain weights were not taken for diploid/tetraploid comparisons because many of the ears were used for self or hand pollinations. The stover was harvested on October 15. All the plants within a line or population in each block were bundled. The bundled plants were taken into a shed and allowed to air dry. On December 8, the plants were weighed.

At Greensburg, Ill., tetraploid populations Synthetic B, OP, CD, ET, and RT and hybrid diploid lines S-57 and S-39 were planted in late May. The planting density was equivalent to 25,344 plants per acre, which was obtained by planting in 30 foot rows at 8 inch spacing.between plantings and a 30 inch spacing between the rows. Each line or population was represented by a single row, and each block was replicated three times. The ears were subject to hand, self, and cross pollinations. The soil at this location is deep, with a high organic content (2%). The area was fertilized with 260 lbs. of 12-12-12 prior to planting. Herbicide application consisted of Sutan ® manufactured by Stauffer Chemical Company and Lasso ® manufactured by Monsanto Agricultural Products Company. On September 24, all the plants within a line or population in each replication were bundled. The bundled plants were taken into a shed and allowed to air dry. On October 22, the plants were weighed. Grain weights were not taken because many of the ears were used for self or hand pollination.

For both the Ohio and Illinois plantings, the stover was chopped for a forage analysis. The forage samples consisted of two samples per line, for each of two blocks. In other words, each line or population had four samples per location. Also, a bulk sample of grain for each line or population was analyzed per two replications. The analyses were done by the Ohio Agricultural Research and Development Center, Wooster, Ohio, and consisted of analysis for percent lignin, hemicellulose, nitrogen, cellulose and calories/gram.

Selections were made within the lines or population on the basis of self-pollinated grain and biomass weights. Those plants with the largest weights were included in a crossing program in Homestead, Fla. which lasted from December 20 until May 20 of the next (second) year. Basically, intercrosses were made between all high yielding tetraploid selections. The tetraploid single crosses generated in Homestead, Fla. were given the designations S-1 through S-12.

The resulting $F_1$ single crosses from this crossing program were used in two plantings in the early summer of the second year. One planting was done on June 2 at the same location as before on the Ohio property. The experiment was a randomized complete block design. Tetraploid lines S-10, S-11 and S-12 were planted along with hybrid diploid lines S-57, S-61 and S-68, which were obtained from the Sohio Agricultural Products Division of Sohio Chemical Corporation. Each block consisted of four treatments: weeded and fertilized; weeded and nonfertilized; nonweeded and fertilized; and nonweeded and nonfertilized. The fertilized plots consisted of 270 lb./acre of nitrogen, phosphorus, and potassium. The weeded plots consisted of 3 lb./acre of Aatrex 80W ® manufactured by Ciba-Geigy Corporation. Fertilizer was applied on June 7; herbicide was applied on June 30.

The planting design consisted of a planting density of 17,400 plants per acre. This was obtained by planting at one foot intervals on 30 foot rows, with the rows being 30 inches apart. Each line was planted in three adjacent rows in each treatment. All measurements were taken on the middle row. Each block was replicated three times.

The other planting was done on June 1 at Arcola, Ill. Tetraploid lines S-1 through S-9 were planted along with hybrid diploid lines S-57, S-61, and S-91, which were obtained from the Sohio Agricultural Products Division of Sohio Chemical Corporation. The experimental design was the same as the Ohio planting. However, the fertilized plots consisted of 150 lb./acre of nitrogen only. The herbicide application consisted of 3 lb./acre of Lasso ® manufactured by Monsanto Agricultural Products Company and 2 lb./acre Aatrex 80W ® manufactured by Ciba-Geigy Corporation.

On August 8 for the Ohio planting, and on August 5 for the Illinois planting, plants were harvested for taking leaf area, stem diameter, and stem height measurements. Three plants per row were measured. The leaf area was taken by removing all leaves from a plant, and calculating the total leaf area using a Leaf Area Meter (Licor, Inc., model 1600). At both locations, all ears were open pollinated. At the Ohio planting, ears were harvested on November 21, and stover was collected according to the method previously described.

The ears were subsequently dried by air drying, and the stover was dried in an "all weather room." At the Illinois planting, the ears were harvested on October 28 and air dried to 15% moisture. The stover was collected on October 28, and fresh weights were taken.

Results and Discussion

The combined results of the first year Ohio and Illinois plantings, the first and second year Florida plantings, and the second year Ohio and Illinois plantings are expressed in Table 1 and Table 2.

Table 1 indicates the mean, standard deviation, coefficient of variability, and number of replications over which the means in the table were calculated for leaf area, stem diameter, stem length, stem area, total plant area, grain weight, stover weight, and total weight. "P" was computed based on the Wilcoxin Signed Rank Test, and represents the probability that the ranks of the means of the diploids and tetraploids were due to chance alone (Steel, R.G. and J.H. Torrie. Principles and Procedures of Statistics, McGraw-Hill, N.Y. (1960) pg. 481, incorporated herein by reference.)

It can be seen from this table that the heterozygous tetraploids, on a per plant basis, were characterized by a greater leaf area, greater stem diameter, shorter stems, greater grain weight, greater stover weight, and greater whole plant weight (combination of grain weight and stover weight) when compared to the hybrid diploids. The diploids were taller than the tetraploids. The means indicated that the tetraploids had a larger overall surface area than the diploids, though this trend was not statistically significant. Furthermore, the percent increase in magnitude of the tetraploid characters over the diploid characters ranged from 3% for total plant surface area to 19% for the stover weight. In terms of total plant weight, the tetraploids averaged 10% greater weight than the diploids.

Table 2 indicates the results of the silage analysis that was done by the Ohio Agricultural Research and Development Center at Wooster. Tests were performed for percent lignin, cellulose, hemicellulose, and nitrogen, in addition to caloric content. It is apparent that the diploids are very similar in their analysis. Because of probable errors in sampling and chemical analysis, no statistical analysis was done on the data. However, two items are particularly noteworthy. The first is that the tetraploids do not differ from the diploids in nutritional quality, especially nitrogen. Secondly, they do not differ appreciably for caloric content. This latter observation is of importance because caloric determinations were done on samples as they were received. In other words, the stover weights and grain weights do not seem to have been biased by differential water retaining capacity. An increase in the water content would result in a lower caloric content.

TABLE 1

| Character | Statistic | Diploid | Tetraploid | Ratio of Tetraploid to Diploid | P |
|---|---|---|---|---|---|
| Leaf Area (cm$^2$) | $\overline{X}$ | 3560.0 | 3708.8 | 1.042 | 0.0228 |
| | SD | 2229.1 | 2157.5 | | |
| | CV | 62.6 | 58.2 | | |
| | N | 30 | 30 | | |
| Stem Diameter (cm) | $\overline{X}$ | 2.5 | 2.7 | 1.080 | 0.0000 |
| | SD | 0.38 | 0.24 | | |
| | CV | 15.5 | 16.1 | | |
| | N | 27 | 27 | | |
| Stem Length (cm) | $\overline{X}$ | 155.0 | 144.4 | 0.93 | 0.0002 |
| | SD | 57.0 | 54.6 | | |
| | CV | 36.7 | 37.8 | | |
| | N | 27 | 27 | | |
| Stem Area (cm$^2$) | $\overline{X}$ | 626.0 | 634.0 | 1.01 | 0.1814 |
| | SD | 293 | 313 | | |
| | CV | 47 | 49 | | |
| | N | 27 | 27 | | |
| Total Plant Area (cm$^2$) | $\overline{X}$ | 4515 | 4637 | 1.027 | 0.1056 |
| | SD | 2386 | 2365 | | |
| | CV | 53 | 51 | | |
| | N | 27 | 27 | | |
| Grain Weight per Plant (gr) | $\overline{X}$ | 75.1 | 78.7 | 1.05 | 0.0047 |
| | SD | 30.3 | 32.0 | | |
| | CV | 40 | 41 | | |
| | N | 27 | 27 | | |
| Stover Weight per Plant (gr) | $\overline{X}$ | 216.2 | 256.2 | 1.185 | 0.0082 |
| | SD | 98.7 | 117.3 | | |
| | CV | 46 | 46 | | |
| | N | 31 | 31 | | |
| Total Weight per Plant (gr) | $\overline{X}$ | 307.5 | 339.1 | 1.102 | 0.0013 |
| | SD | 102.7 | 128.5 | | |
| | CV | 33 | 38 | | |
| | N | 26 | 26 | | |

$\overline{X}$ represents the mean of the character
SD represents the standard deviation of the character
CV represents the coefficient of variation of the character
N represents the number of replications, over all treatments and locations, which were used to calculate the $\overline{X}$, SD, and CV
P represents the probability that the ranks of the means of the diploids and tetraploids were due to chance alone, according to the Wilcoxin Signed Rank Test (Steel and Torrie, 1960)

TABLE 2

Stover silage analysis done on plants of the Sagamore Hills and Greensburg plantings. Means are based on pooled means of diploids and tetraploids, over each of two replications in both locations. The grain analysis is similar, but is based only on the replications at the Greensburg planting.

| Character | Statistic | Diploid | Tetraploid |
|---|---|---|---|
| Percent Lignin: | | | |
| Stover | $\overline{X}$ | 5.4 | 6.6 |

TABLE 2-continued

Stover silage analysis done on plants of the Sagamore Hills and Greensburg plantings. Means are based on pooled means of diploids and tetraploids, over each of two replications in both locations. The grain analysis is similar, but is based only on the replications at the Greensburg planting.

| Character | Statistic | Diploid | Tetraploid |
|---|---|---|---|
| | SD | 1.0 | 1.3 |
| | N | 4 | 4 |
| Grain | X̄ | 3.4 | 3.1 |
| | SD | 0.57 | 0.99 |
| | N | 2 | 2 |
| Percent Cellulose: | | | |
| Stover | X̄ | 43.0 | 41.5 |
| | SD | 0.70 | 3.9 |
| | N | 4 | 4 |
| Grain | X̄ | 2.6 | 4.1 |
| | SD | 1.13 | 0.85 |
| | N | 2 | 2 |
| Percent Hemi-Cellulose: | | | |
| Stover | X̄ | 51.6 | 51.6 |
| | SD | 1.1 | 2.8 |
| | N | 4 | 4 |
| Grain | X̄ | 94.1 | 92.8 |
| | SD | 0.49 | 0.8 |
| | N | 2 | 2 |
| Percent Nitrogen: | | | |
| Stover | X̄ | 1.0 | 1.3 |
| | SD | 0.15 | 0.21 |
| | N | 4 | 4 |
| Grain | X̄ | 1.7 | 2.0 |
| | SD | 0.07 | 0.00 |
| | N | 2 | 2 |
| Calories/Gram: | | | |
| Stover | X̄ | 4171.6 | 4151.7 |
| | SD | 91.5 | 73.6 |
| | N | 4 | 4 |
| Grain | X̄ | 4257.8 | 4328.0 |
| | SD | 23.1 | 9.48 |
| | N | 2 | 2 |

X̄, SD, and N have the same meaning as they do in TABLE 1.

EXAMPLE II

In May, seeds of Dudley and Alexander's "Synthetic B" were obtained from the University of Illinois and planted at Sagamore Hills, Ohio. Self-pollinations were made on the most robust plants during the summer. Self-pollinated seeds from these plants were bulked and selfed in the succeeding three winters and the summer following the last winter. Ears were kept separate from the last summer planting, and an ear-to-row planting was made during the following winter. Acceptable uniformity was observed for several of the inbred lines, one of which was designated X-4-2. X-4-2 is a tetraploid Zea maize ssp. maize.

X-4-2 has the following characteristics. It is a dent corn adapted for most regions of the United States. The plant is 136 cm high and has 1 tiller and 1 ear per stalk. The ear height is 51 cm. The leaf is dark green and at an angle of less than 30° from the stalk. Sheath pubesence is light and there are few marginal waves. Longitudinal creases are absent. Leaf width is 9 cm at the widest point of the ear node leaf, and the length of the ear node leaf is 71 cm. The tassel has 7 lateral branches with a branch angle from the central spike greater than 45°. The pollen shed is heavy. The anther, glume, and ring color is yellow. The exposed silk color and the internal silk color is green. The husk color is dark green when the husk is fresh. The husk extension is greater than 10 cm at the harvest stage and the husk leaf is less than 8 cm. The husked ear is 15 cm in length. with 18 kernel rows, and the cob color is red.

| Outline of the Development of X-4-2 | | | |
|---|---|---|---|
| Type | Description | Location | Year |
| Synthetic B | Self-pollination | Ohio, Illinois | 1 |
| 4 | Self-pollination | Florida | 1-2 |
| 4 | Self-pollination | Florida | 2-3 |
| 4 | Self-pollination | Florida | 3-4 |
| 4 | Self-pollination | Florida | 4 |
| X-4-2 | Self-pollination | Florida | 4-5 |

EXAMPLE III

In May, seeds of Dudley and Alexander's "Synthetic obtained from the University of Illinois and planted at Sagamore Hills, Ohio. Self-pollinations were made on the most robust plants during the summer. Self-pollinated seed from these plants were bulked and selfed in the following three winters and the summer following the last winter. Ears were kept separate from the last summer planting, and an ear-to-row planting was made during the following winter. Acceptable uniformity was observed for several of the inbred lines, one of which was designated X-5-6. X-5-6 is a tetraploid Zea maize ssp. maize.

X-5-6 has the following characteristics. It is a dent corn adapted for most regions of the United States. The plant is 155 cm high and has 1 tiller and 1 ear per stalk. The ear height is 60 cm. The leaf is dark green and at an angle of less than 30° from the stalk. Sheath pubesence is medium. There are few marginal waves and few longitudinal creases. Leaf width is 14 cm at the widest point of the ear node leaf, and the length of the ear node leaf is 70 cm. The tassel has 14 lateral branches with a branch angle from the central spike less than 30°. The pollen shed is heavy. The anther color is yellow. The glume color and the ring color are pink. The exposed silk color and the internal silk color is green. The husk color is dark green when the husk is fresh. The husk extension is 8-10 cm beyond ear tip at the harvest stage. The husk leaf is less than 8 cm. The husked ear is 18 cm in length with 12 kernel rows, and the cob color is pink.

| Outline of the Development of X-5-6 | | | |
|---|---|---|---|
| Type | Description | Location | Year |
| Synthetic OP | Self-pollination | Ohio, Illinois | 1 |
| 5 | Self-pollination | Florida | 1-2 |
| 5 | Self-pollination | Florida | 2-3 |
| 5 | Self-pollination | Florida | 3-4 |
| 5 | Self-pollination | Indiana | 4 |
| X-5-6 | Self-pollination | Florida | 4-5 |

EXAMPLE IV

In May, seeds of Dudley and Alexander's "Synthetic CD" were obtained from the University of Illinois and planted at Sagamore Hills, Ohio. Self-pollinations were made on the most robust plants during the summer. Self-pollinated seed from these plants were bulked and selfed in the succeeding three winters and the summer following the last winter. Ears were kept separate from the last summer planting, and an ear-to-row planting was made during the following winter. Acceptable uniformity was observed for several of the inbred lines, one of which was designated X-6-3. X-6-3 is a tetraploid Zea maize ssp. maize.

X-6-3 has the following characteristics. It is a dent corn adapted for most regions of the United States. The plant is 132 cm high and has 1 tiller and a tendency toward 2 ears per stalk. The ear height is 50 cm. The leaf is dark green and at an angle of greater than 60° from the stalk. Sheath pubesence is light and there are few marginal waves. Longitudinal creases are absent. Leaf width is 9 cm at the widest point of the ear node leaf, and the length of the ear node leaf is 55 cm. The tassel has 8 lateral branches with a branch angle from the central spike less than 30°. The pollen shed is heavy. The anther, glume, and ring color is pink. The exposed silk color and the internal silk color is green. The husk color is dark green when the husk is fresh. The husk extension is greater than 10 cm at the harvest stage. The husk leaf is less than 8 cm.

| Outline of the Development of X-6-3 | | | |
|---|---|---|---|
| Type | Description | Location | Year |
| Synthetic CD | Self-pollination | Ohio, Illinois | 1 |
| 6 | Self-pollination | Florida | 1–2 |
| 6 | Self-pollination | Florida | 2–3 |
| 6 | Self-pollination | Florida | 3–4 |
| 6 | Self-pollination | Indiana | 4 |
| X-6-3 | Self-pollination | Florida | 5 |

EXAMPLE V

In November, 20 seeds of X-5-6 and 20 seeds of X-6-3 were planted in two rows alongside each other in Homestead, Fla. Conventional applications of fertilizers and pesticides were made. In March of the next year, tassle bags were placed over the tassles of the X-5-6 plants, and ear shoot bags were placed over the ear shoots of the X-6-3 plants on the same day. The next day, the ear shoot bags were removed, pollen collected in the tassle bags was sprinkled on the silks of the X-6-3 plants, and the tassel bags were secured over the ear shoots. Approximately, 42 days later, the hybrid seeds were harvested.

In May, the seeds were planted ear to row in North Platte, Nebr. in a yield trial. At maturity, the hybrid plants will be evaluated for height, total plant dry weight, weight of ears, and grain weight.

It will be apparent to those skilled in the art that various modifications and variations can be made in the processes and products of the present invention. Thus, it is intended that the present invention cover modifications and variations of this invention, provided that they come within the scope of the appended claims and their equivalents.

What is claimed is:

1. An inbred line of tetraploid corn wherein said inbred line has the characteristics of SX-4-2, SX-4-4, SX-4-16-2, SX-4-32-1, SX-4-33-4-2, SX-5-6, SX-5-11, SX-5-9-1-2, SX-5-13-3, SX-5-14-1-2, SX-6-3, or SX-6-15-2-1.

2. The inbred line of claim 1 wherein said line has the characteristics of SX-4-2.

3. The inbred line of claim 1 wherein said line has the characteristics of SX-4-4.

4. The inbred line of claim 1 wherein said line has the characteristics of SX-4-16-2.

5. The inbred line of claim 1 wherein said line has the characteristics of SX-4-32-1.

6. The inbred line of claim 1 wherein said line has the characteristics of SX-4-33-4-2.

7. The inbred line of claim 1 wherein said line has the characteristis of SX-5-6.

8. The inbred line of claim 1 wherein said line has the characteristics of SX-5-11.

9. The inbred line of claim 1 wherein said line has the characteristics of SX-5-9-1-2.

10. The inbred line of claim 1 wherein said line has the characteristics of SX-5-13-3.

11. The inbred line of claim 1 wherein said line has the characteristics of SX-5-14-1-2.

12. The inbred line of claim 1 wherein said line has the caharacteristics of SX-6-3.

13. The inbred line of claim 1 wherein said line has the characteristics of SX-6-15-2-1.

14. A process for producing a seed of an inbred line of tetraploid corn comprising the steps of:
self-pollinating an inbred line of tetraploid corn; and
harvesting a seed produced by said self-pollinating, wherein said inbred line has the characteristics of SX-4-2, SX-4-4, SX-4-16-2, SX-4-32-1, SX-4-33-4-2, SX-5-6, SX-5-11, SX-5-9-1-2, SX-5-13-3, SX-5-14-1-2, SX-6-3, or SX-6-15-2-1.

15. A seed of an inbred line of tetraploid corn produced by the process of claim 14.

16. A seed of an inbred line of tetraploid corn wherein said inbed line has the characteristis of SX-4-2, SX-4-4, SX-4-16-2, SX-4-32-1, SX-4-33-4-2, SX-5-6, SX-5-11, SX-5-9-1-2, SX-5-13-3, SX-5-14-1-2, SX-6-3, or SX-6-15-2-1.

17. The seed of claim 16 wherein said seed is produced by an inbred tetraploid corn line having the characterized of SX-4-2.

18. The seed of claim 16 wherein said seed is produced by an inbred tetraploid corn line having te characteristic of SX-4-4.

19. The seed of claim 16 wherein said seed is produced by an inbred traploid corn line having the characteristics of SX-4-16-2.

20. The seed of claim 16 wherein said seed is produced by an inbred tetrapoloid corn line having the characteristics of SX-4-32-1.

21. The seed of claim 16 wherein said seed is produced by an inbred tetraploid corn line having the characteristiscs of SX-4-33-4-2.

22. The seed of claim 16 wherein said seed is produced by an inbred tetraploid corn line having the characteristics of SX-5-6.

23. The seed of claim 16 wherein said seed is produced by an inbred tetraploid corn line having the chasracteristics of SX-5-11.

24. The seed of claim 16 wherein said seed is produced by an inbred tetraploid corn line having the characteristics of Sx-5-9-1-2.

25. The seed of claim 16 wherein said seed is produced by an inbred teraploid corn line having the characteristics of SX-5-13-3.

26. The seed of claim 16 wherein said seed is produced by an inbred tetraploid corn line having the characteristics of SX-5-14-1-2.

27. The seed of claim 16 wherein said seed is produced by an inbred tetraploid corn line having the characteristics of SX-6-3.

28. The seed of claim 16 wherein said seed is produced by an inbred tertraploid corn line having the characteristics of SX-6-15-2-1.

29. A process for producing a hybrid tetraploid corn seed comprising the steps of:

crossing a first inbred line of tetraploid corn with a nonidentical second line of tetraploid corn to produce a seed; and harvesting said seed, wherein said nonidenticasl inbred lines have the characteristics of SX-4-2, SX-4-4, SX-4-16-2, SX-4-32-1, SX-4-33-4-2, SX-5-6, SX-5-11, SX-5-9-1-2, SX-5-13-3, SX-5-14-1-2, SX-5-14-1-2, SX-6-3, or SX-6-15-2-1.

30. A process for producing a hybrid tetraploid corn seed comprising steps of:

developing inbred lines of tetraploid corn which, upon cross-fertilzation, yield $F_1$ hybrid seeds that produce hybrid tetraploid corn plants having desired characteristics;

crossing any two nonidentical lines of said inbred lines to produce an $F_1$ hybrid seed; and harvesting said seed, wherein said nonidentical inbred lines have the characteristics of SX-4-2, SX-4-4, SX-4-16-2, SX-4-32-1, SX-4-33-4-2, SX-5-6, SX-5-11, SX-5-9-1-2, SX-5-13-3, SX-5-14-1-2, SX-6-3, or SX-6-15-2-1.

31. A hybrid tetraploid corn seed produced by the process of claims 29 or 30.

32. A hybrid tetraploid corn seed wherein said seed is a seed of an $F_1$ hybrid plant, the parents of said plant being nonidenticasl inbred lines of tetraploid corn having the characteristics of SX-4-2, SX-4-4, SX-4-16-2, SX-4-32-1, SX-4-33-4-2, SX-5-6, SX-5-11, SX-5-9-1-2. SX-5-13-3, SX-5-14-1-2, SX-6-3, or SX-6-15-2-1.

33. A hybrid tetraploid corn plant produced by growing a seed produced by the process of claims 29, 30 or 32.

34. A process for producing a hybrid tetraploid corn plant comprising the steps of:

crossing a first inbred line of tetraploid corn with a nonidentical second inbred line of tetraploid corn to produce a hybrid seed; and harvesting and growing said hybrid seed to produce said hybrid plant, wherein said nonidentical first and second lines the characteristics of SX-4-2, SX-4-4, SX-4-16-2, SX-4-16-2, SX-4-32-1, SX-4-33-4-2, SX-5-6, SX-5-11, SX-5-9-1-2, SX-5-13-3, SX-5-14-1-2, SX-6-3, or SX-6-15-2-1.

35. A hybrid tetraploid corn plant produced by the process of claim 34.

36. A hybrid tetraploid corn zygote produced by the process of crossing a first inbred line of tetraploid corn with a nonidentical second inbred lline to form a hybrid tetraploid zygote and recovering said zygote, wherein said nonidentical inbred lines have the characteristics of SX-4-2, SX-4-4, SX-4-16-2, SX-4-32-1, SX-4-33-4-2, SX-5-6, SX-5-11, SX-5-9-1-2, SX-5-13-3, SX-5-14-1-2, SX-6-3, or SX-6-15-2-1.

* * * * *